US00PP24056P3

(12) United States Plant Patent
Brown

(10) Patent No.: US PP24,056 P3
(45) Date of Patent: Dec. 3, 2013

(54) ***WESTRINGIA FRUTICOSA* PLANT NAMED 'NFL21'**

(50) Latin Name: *Westringia fruticosa*
Varietal Denomination: NFL21

(76) Inventor: Graham Brown, Pennant Hills (AU)

( * ) Notice: Subject to any disclaimer, the term of this patent is extended or adjusted under 35 U.S.C. 154(b) by 85 days.

(21) Appl. No.: 13/374,813

(22) Filed: Jan. 17, 2012

(65) Prior Publication Data

US 2013/0185835 P1 Jul. 18, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Sam McCoy

(57) ABSTRACT

'NFL21' is a distinctive variety of *Westringia fruticosa* which is characterized by the combination of an upright and dense growth habit, tall plant height, highly pubescent leaves and purple flower color.

2 Drawing Sheets

Latin name of the genus and species: The Latin name of the genus and species of the novel variety disclosed herein is *Westringia fruticosa.*

Variety denomination: The inventive variety of *Westringia* disclosed herein has been given the variety denomination 'NFL21'.

BACKGROUND OF THE INVENTION

The present invention relates to a new and distinct perennial variety of *Westringia fruticosa*, which has been given the variety denomination of 'NFL21'. Its market class is that of an ornamental shrub. 'NFL21' is intended for use in landscaping for hedges or as specimen plants for home gardens.

Parentage: The *Westringia fruticosa* variety 'NFL21' was finally selected in 2009 in an Australian nursery in Cobbitty, New South Wales following a selection process carried out from 2005 to 2008 involving approximately 1000 seedlings of common *Westringia fruticosa* (unpatented) production stock. 'NFL21' is a seedling selection from open pollinated *Westringia fruticosa*. 'NFL21' was initially selected for to its dense, upright habit and vigorous growth rate.

Asexual Reproduction: 'NFL21' was first propagated asexually by division at a wholesale nursery in Richmond, New South Wales, Australia. The distinctive characteristics of the inventive 'NFL21' variety are stable from generation to generation; clones of the variety produced by asexual reproduction maintain the distinguishing characteristics of the original plant.

A Provisional Patent application for variety 'NFL21' was filed with the US Patent and Trademark Office on Jan. 21, 2010 under Application No. 61/461,615.

SUMMARY OF THE INVENTION

'NFL21' is a distinctive variety of *Westringia fruticosa* which is characterized by the combination of an upright and dense growth habit, tall plant height, highly pubescent leaves and purple flower color.

BOTANICAL DESCRIPTION OF THE PLANT

Figure 1:
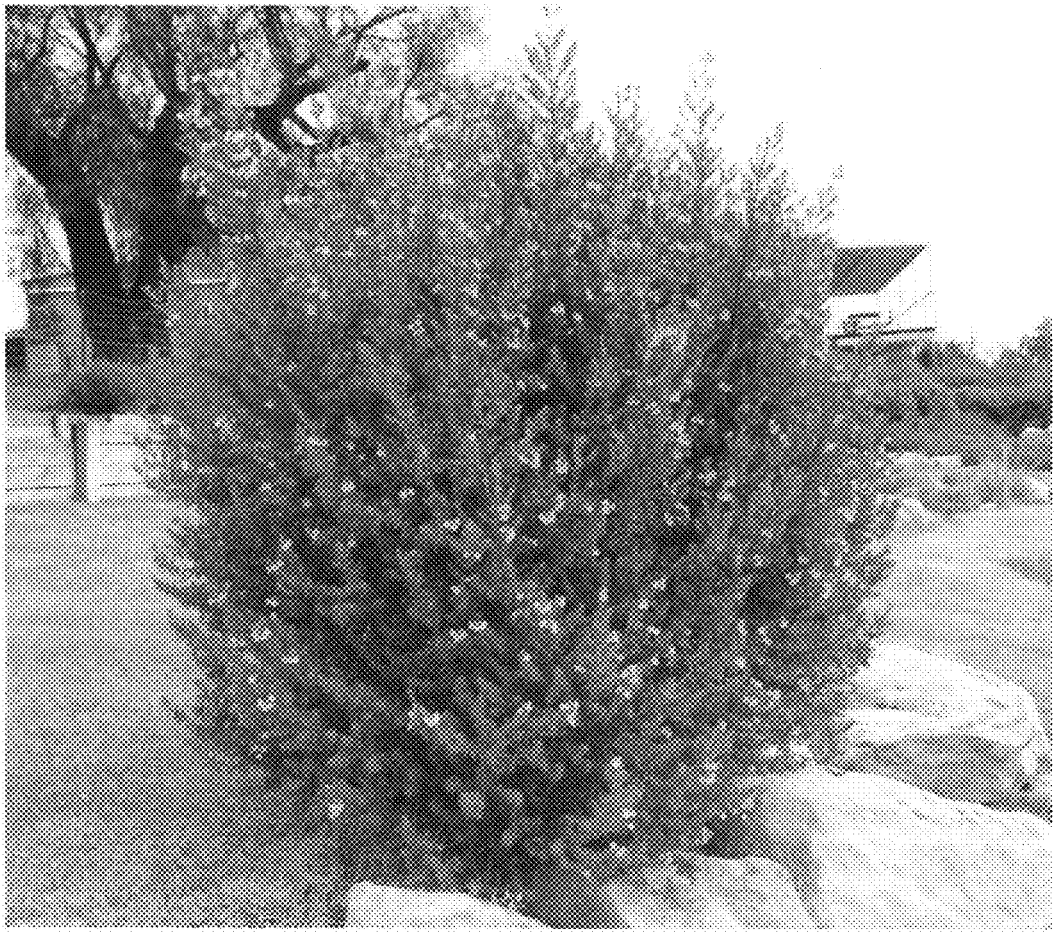
FIG. 1 shows a 3-year old, mature 'NFL21' plant, unpruned, in flower.
Figure 2:
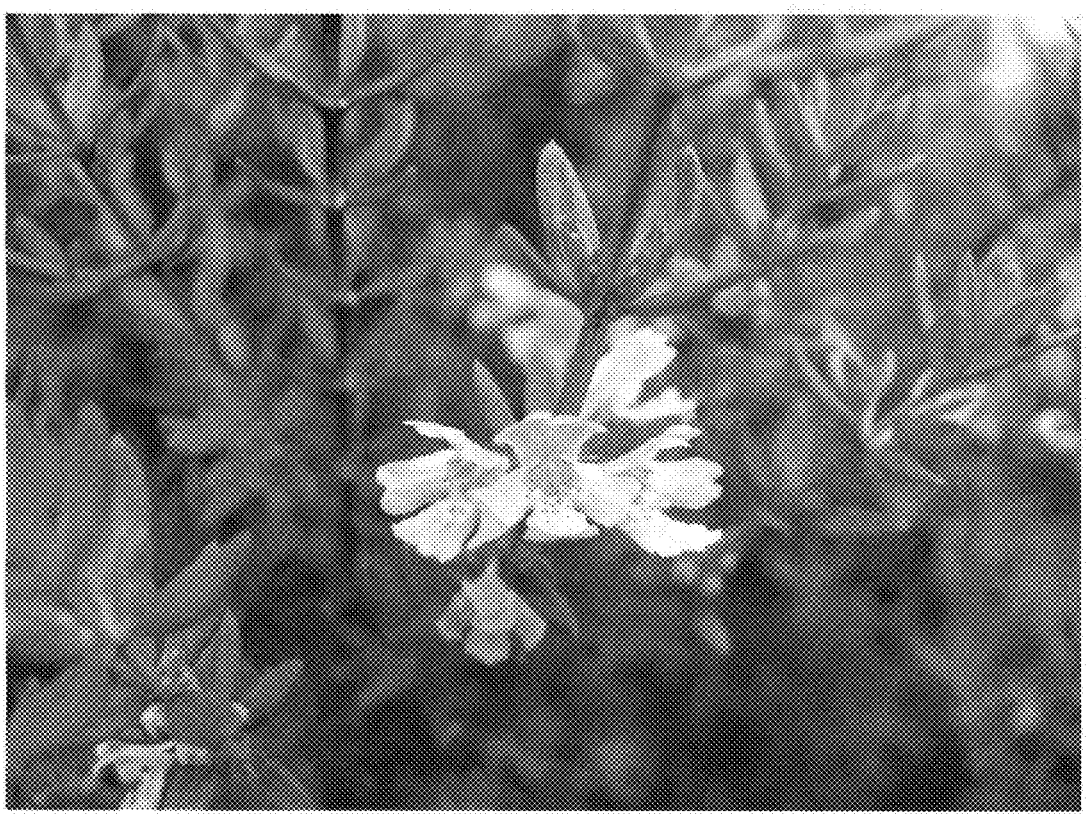
FIG. 2 shows a macro view of the 'NFL21' flower. Also of note is a heavy leaf pubescence.

The following is a detailed botanical description of a new and distinct variety of a *Westringia fruticosa* ornamental plant known as 'NFL21'. Plant observations were made on plants grown in New South Wales, Australia. Unless indicated otherwise, the descriptions disclosed herein are based upon observations made in October 2010 of mature 'NFL21' plants grown in nursery pots.

Those skilled in the art will appreciate that certain characteristics will vary with older or, conversely, younger plants. 'NFL21' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 2001 edition. Note that generic color descriptions such as 'purple' do not exist in the R.H.S. charts and the corresponding R.H.S. colors are quoted.

'NFL21' is a seedling selection from a *Westringia fruticosa* (unpatented) which is characterized by the combination of an upright and dense growth habit, tall plant height, highly pubescent leaves and purple flower color.

These features and other characteristics are apparent from the description provided below.

Growth Habit, Dimensions and Color

Plant description:

*Bloom period.*—Spring with sporadic flowering in fall.
*Plant habit.*—Shrub; upright, erect and dense.
*Height.*—200 to 225 cm at maturity (observed in October 2011).
*Width.*—100 to 125 cm at maturity (observed in October 2011).
*Hardiness.*—USDA Zone 9 to 11.

*Propagation.*—Propagation is accomplished using semi-hard wood cuttings. Roots well without rooting compound or hormone.

*Time to develop roots.*—Approximately 3 weeks.

*Crop time.*—From approximately five to six months are needed to produce a 14-centimeter container with plant in flower, starting from a rooted cutting and depending on location and production practices.

*Pest and disease susceptibility or resistance.*—In common with the species, none of note.

Roots: The roots of 'NFL21' are colored white and fleshy and thick, similar to other *Westringia fruticosa.*

Stem:

*Shape.*—Cylindrical yet angular.

*Stem color.*—Young stem is closest to green 138B.

*Stem dimensions.*—Some mature stems can reach 110 cm in length with a diameter of 12 to 15 mm near the base.

*Stem surface.*—Corky and pruinose.

*Basal stem color.*—Predominantly brown 200A with striations of both grey brown 199D and green 138A at maturity.

*Branching and habit.*—Strong branching habit; branch angles highly acute.

*Internode length.*—10.5 mm on average.

Foliage:

*Type.*—Evergreen.

*Shape.*—Elliptical, narrow.

*Division.*—Simple.

*Apex.*—Acute.

*Base.*—Cunneate.

*Venation.*—Pinnate.

*Vein color.*—Indistinguishable from lamina, from both the adaxial and abaxial aspect.

*Margins.*—Entire.

*Arrangement.*—Whorled.

*Attachment.*—Petiolate.

*Surface texture* (*adaxial surface*).—Hoary.

*Surface texture* (*abaxial surface*).—Hoary to canescent.

*Mature leaf dimensions.*—Ranges from 16 to 21 mm, width ranges from 3.5 to 6 mm.

*Leaf color* (*adaxial surface*).—Juvenile: 138B; mature: 139B.

*Leaf color* (*abaxial surface*).—Juvenile: 138B; mature: 138B.

*Petiole.*—Approximately 2 to 3 mm in length; width is approximately 1 mm.

*Stipules.*—Laminar and green (RHS 138A); pubescent; length is approximately 2 to 4 mm.

Inflorescence: Flowers are sessile, singular and persist for approximately 5 days. Self cleaning. Non fragrant.

Bud: Oblong to globose in shape and rounded at the apex. Approximately 6 mm long and 3 mm wide prior to dehiscence. Color is violet 85B.

Flowers: Sympetalous, irregular with sepal lobes appearing to number four, width across the corolla measuring on average 14 mm and a length of 19 mm; color approximates to 76A. Calyx is synsepalous with five calyx lobes; green (RHS 137C).

Reproductive organs:

*Stamens.*—4.

*Stamen color.*—76A.

*Stamen dimensions.*—About 3 mm in length and very thin.

*Attachment.*—Each stamen joins floral tube independently: Free.

*Anther dimensions.*—Minute.

*Anther color.*—Yellow.

*Pollen.*—Absent.

*Pistil.*—One.

*Pistil dimensions.*—About 8 mm. in length and very thin.

*Pistil color.*—76A.

*Ovary position.*—Half-Inferior.

Fruit and seed production: Not yet observed.

Comparison of NFL21 with Other Varieties of *Westringia fruticosa*

When compared to the parent, 'NFL21' is taller and has a narrower plant width, shorter internodes and purple flower. 'NFL21' has a mature plant height of approximately 200 to 225 cm whereas *Westringia fruticosa* (unpatented) grows to approximately 160 to 180 cm. 'NFL21' has a mature width of approximately 100 to 125 cm whereas *Westringia fruticosa* (unpatented) has an open growth habit and can spread to 300 cm or more if left unpruned. 'NFL21' has an average internode length of 10.5 mm whereas *Westringia fruticosa* (unpatented) has internodes ranging in length from 11 to 15 mm. 'NFL21' has a dense branching habit whereas the parent is less dense. 'NFL21' has a purple flower color corresponding to RHS 76 A whereas common *Westringia fruticosa* has a flower color corresponding to white RHS 157.

'NFL21' is similar in form and function to *Westringia* hybrid 'Wynyabbie Gem' (not patented) in that both have dense foliage, a dense branching habit and a flower color that would generally be referred to as "purple". However 'NFL21' has an upright habit whereas 'Wynyabbie Gem' has a semi-upright and rounded habit. 'NFL21' has mature height and width dimensions of approximately 200 to 225 cm by 100 to 125 cm, respectively, whereas 'Wynyabbie Gem' has dimensions of approximately 100 to 150 cm tall and 100 to 150 cm wide. 'NFL21' has a purple flower corresponding to RHS 76A whereas the flowers of 'Wynyabbie Gem' are violet corresponding to RHS 85C.

In terms of growth habit and flower color, 'NFL21' is most similar to *Westringia* hybrid 'WES01' (AU PBR 2008/311, unpatented in the US) in that both are upright, dense and both have a violet flower. However, 'NFL21' is a larger plant, with shorter internodes, branch angles that are more acute, and heavy leaf pubescence. 'NFL21' can grow to approximately 200 to 225 cm tall whereas 'WES01' grows to approximately 180 cm tall. The internodes of 'NFL21' are, on average, 10.5 mm whereas the internodes of 'WES01' are 13.8 mm, on average, which gives 'NFL21' a more dense appearance. Both 'NFL21' and 'WES01' have upright growth habits, however the branch angles of 'NFL21' are more acute than those of 'WES01' which gives 'NFL21' a tighter, more compact habit. The leaf color of both 'NFL21' and 'WES01' is green (RHS 139B and RHS 137D, respectively) however 'NFL21' has moderate to heavy leaf pubescence on the adaxial leaf surface whereas 'WES01' has weak leaf pubescence. The resulting affect is that 'NFL21' with the higher density of white hairs and the slightly more saturated hue of green in the leaf gives 'NFL21' a gray-green look whereas 'WES01', in general terms, appears to have a yellow green color.

The combination of an upright and dense growth habit, tall plant height, highly pubescent leaves and purple flower color makes 'NFL21' a desirable ornamental plant suited for mass production for pot and landscape use.

That which is claimed is:

1. A new and distinct variety of *Westringia fruticosa* plant named 'NFL21', substantially as described and illustrated herein.

* * * * *